United States Patent [19]

Gasser et al.

[11] Patent Number: 5,137,664
[45] Date of Patent: Aug. 11, 1992

[54] PROCESS FOR THE TREATMENT OF DENTAL IMPRESSIONS

[75] Inventors: Oswald Gasser, Seefeld; Klaus Ellrich, Worthsee, both of Fed. Rep. of Germany

[73] Assignee: ESPE Stiftung & Co. Produktions-und Vertriebs KG, Seefeld, Fed. Rep. of Germany

[21] Appl. No.: 411,037

[22] Filed: Sep. 21, 1989

[30] Foreign Application Priority Data

Sep. 23, 1988 [DE]  Fed. Rep. of Germany ....... 3832417

[51] Int. Cl.$^5$ .......................... A61C 16/00; B28B 7/36
[52] U.S. Cl. ........................................ 264/39; 264/16; 264/338; 264/340; 427/2; 427/133
[58] Field of Search ........................ 264/16, 17, 19, 39, 264/226, 337, 338, 340, 341, 343; 433/201.2, 202.1, 217.1, 213, 223, 214, 171, 199.1; 424/673; 249/54, 114.1; 106/35, 38.2, 38.22; 252/79.3; 427/2, 133; 134/26, 29

[56] References Cited

U.S. PATENT DOCUMENTS 4,076,779  2/1978  Skriletz .................................. 264/39
4,810,294  3/1989  Yagi et al. ............................. 106/35

Primary Examiner—Jan H. Silbaugh
Assistant Examiner—Christopher A. Fiorilla
Attorney, Agent, or Firm—Birch, Stewart, Kolasch & Birch

[57] ABSTRACT

The invention relates to a process for the treatment of dental impressions of conventional molding material, in which the surface of the impressions is treated prior to filling with plaster with an aqueous solution which contains 0.01 to 10 % by weight of a fluorine compound. The detrimental effect which the surface-active substances adhering to the dental impressions have on the surface finish of the plaster models which are produced using the dental impressions is thus eliminated.

10 Claims, No Drawings

PROCESS FOR THE TREATMENT OF DENTAL IMPRESSIONS

BACKGROUND OF THE INVENTION

The production of dentures in the dental laboratory usually takes place using a working model which reproduces the tooth and jaw ratios of the patient as faithfully as possible. The dentist in attendance initially takes a negative impression using elastic molding materials which are distinguished by high molding accuracy, high form-retention and good reproduction of details. Such molding materials are, for example, the so-called reversible hydrocolloids of an agar-agar base, irreversible hydrocolloids of an alginate base, polysulfides, polyethers and silicones cross-linked by condensation and addition.

Dental impressions, which are also known as negative molds, thus obtained can then be filled with a molding material by the dentist or dental technician and thus provide the working model. As the molding materials, plasters in particular are available which can differ greatly with regard to their quality and price. Here, it is of course true that the higher-quality plasters, which also have a good surface-finish, are comparatively expensive.

Attempts have therefore already been made to improve models produced from cheaper types of plaster by surface treatments. This can be effected, for example, by the application of a hardenable lacquer. This is not however a satisfactory solution as a rule, because the hardening coating allows only poor adhesion to the plaster and in addition the accuracy of the model material is affected by the coating applied.

A further problem related to the surface quality of these plasters is the negative effect of the surface-active substances which can be present on the surface of the negative molds. The use of these surface-active substances, or surfactants, is necessary if the negative mold has to be thoroughly cleaned, disinfected or its surface tension reduced. The surface-active substances become concentrated on the surface of the negative molds, made, for example from hydrocolloids and despite rinsing cannot be completely removed. This leads ultimately to an impairment of the surface quality of the plaster and therefore to an impairment of the molding accuracy of the plaster model.

It is known from "The Science of Dental Materials", 5th edition, 1960, W.B. Saunders Company, Philadelphia and London, to add, inter alia. fluorine compounds to the molding materials to increase the surface hardness of the plaster molds so produced (see page 94). The detrimental effect of the surface-active substances which adhere to the impressions is not however influenced by this. When cheaper types of plaster are employed, even if molding materials containing fluorine compounds are used, one ultimately obtains plaster models which have sandy surfaces and whose contour definitions leave much to be desired.

SUMMARY OF THE INVENTION

It is therefore the object of the invention to find a way of preventing the detrimental effect on the surface-finish of the plaster of the surface-active substances which adhere to the negative molds.

This object is achieved by treating the surface of the dental impressions, or negative molds, with an aqueous solution which contains 0.01 to 10 % by weight of a fluorine compound The amount of fluorine compound in the solution is preferably 0.1 to 5% by weight and particularly 0.5 to 2% by weight.

DETAILED DESCRIPTION

The following come into consideration as fluorine compounds: inorganic fluorine compounds which have solubilities within the specified concentration ranges, such as metal fluorides, e.g. the alkali fluorides, magnesium fluoride, zinc fluoride or stannic fluorides or complex fluorine compounds, containing metals of the third to fifth main group and also metals of the subgroups and rare earth elements of the chemical periodic system. Preferred are sodium zinc fluoride and particularly complex fluorine compounds of the formula $A_2MF_6$, in which A preferably represents an alkali metal, particularly sodium or potassium, and M represents silicon, tin, titanium, zirconium or hafnium. Particularly suitable complex fluorine compounds are $K_2TiF_6$ and $K_2ZrF_6$.

The concentration of the fluorine compound in the solution depends on the intended use, solubility and stability of the fluorine compound and can be optimized for each case using few tests. Using complex fluorine compounds, such as for example $K_2TiF_6$ and $K_2ZrF_6$, a concentration range of 0.5 to 2% by weight has proved particularly favorable.

The solutions to be used according to the invention can also contain additives to make them suitable for simultaneous use as cleaning solutions, disinfectant solutions or surface-tension reducing sprays. For example, disinfectants such as quaternary ammonium compounds, organic per-acids, e.g. peracetic acid, aldehydes, e.g. glutaraldehyde and glyoxal, phenols and alcohols and other known disinfectants are suitable additives. In addition, small amounts of surface-active substances can be present, for example surfactants from the group of the non-ionic and anionic surfactants. In addition, fragrances and flavorings, colorants, antioxidants and, optionally, indicators can be added.

In the implementation of the process according to the invention the solutions can be sprayed, for example, in the form of sprays containing at least one of the specified fluorine compounds. The use of dipping baths which contain a fluorine compound in the concentration range given above is also advantageous.

When dipping baths are used, the negative mold is advantageously dipped into the solution for a short period of time. Possible dipping periods are from 5 seconds to 30 minutes. The period of dipping however depends very much on the intended effect. If the intention is simultaneously to clean and disinfect, then dipping periods of 1 to 20, particularly 5 to 15 minutes are suitable. To ensure dimension stability, particularly of the irreversible-hydrocolloid negative molds, it is useful that, small amounts, e.g. 1 to 10% by weight, of alcohols are present in addition to the disinfectant, e.g. a mixture of glutaraldehyde and glyoxal so that negative molds made of hydrophilic impression materials do not undergo any swelling or shrinkage during disinfection.

The production of the solutions to be used according to the invention is carried out in a simple manner by dissolution in water, and possibly alcohol, of the appropriate amount of fluorine compound for the desired concentrations. For example, an aqueous or aqueous/alcoholic solution containing 0.01 to 10% by weight of fluorine compound can be used as the dipping or spray solution for treating the negative molds. When the process according to the invention is carried out using a disinfectant solution the fluorine compound is dissolved at the desired concentration in an aqueous or aqueous-/alcoholic disinfectant mixture. Here it may possibly be advantageous to add surfactants simultaneously to increase the disinfectant effect. The detrimental effect of the surfactant on the surface of the plaster molds produced using the negative molds is eliminated by the fluorine compound to be used according to the invention.

EXAMPLE 1

Production of a dipping solution.

0.5 parts by weight of $K_2TiF_6$ are stirred in 99.5 parts by weight of distilled water until a homogeneous clear solution is formed.

EXAMPLE 2

An upper jaw impression (negative mold) taken from a subject using an alginate molding material, obtained from a mixture of 40 parts by weight of tap water and 20 parts by weight of alginate impression powder, consisting of 11% potassium alginate, 19.5% calcium sulphate, 3.7% tetrasodium diphosphate, 2.8% potassium titanium fluoride, 60% kieselguhr, 1% of pyrogenic silicon dioxide and 2% of zinc oxide, is immersed completely for a period of 10 seconds in a dipping bath consisting of a 500 ml solution as in Example 1. For comparison purposes a second impression from the same molding material is taken from the same patient, but not dipped. Both impressions are then filled with a dental plaster (Moldano, Bayer). The plaster is left in the impression for 30 minutes and is then carefully removed from the alginate impression. In the case of the plaster model removed from the impression which was not dipped (comparison test) a relatively rough surface with a sandy effect is obtained, while a thin coating of blue plaster material which has not hardened remains on the alginate impression. In the case of the plaster model removed from the impression which was dipped, a smooth, hard surface is obtained and the remaining impression shows no residue at all of unhardened plaster.

EXAMPLE 3

Production of a disinfectant solution.

99.5 parts by weight of a disinfectant, containing 0.9% by weight of glutaraldehyde, 1.8% by weight of glyoxal, 4.5% by weight of ethanol and the rest water, is stirred with 0.5 parts by weight of sodium fluoride until a homogeneous clear solution is formed.

EXAMPLE 4

Production of a disinfectant solution.

99.5 parts by weight of a disinfectant, containing 0.9% by weight of glutaraldehyde, 1.8% by weight of glyoxal, 4.5% by weight of ethanol and the rest water, are stirred with 0.5 parts by weight of $K_2TiF_6$ until a homoqeneous clear solution is formed.

EXAMPLE 5

Alginate impressions are taken from subjects following the same procedure as in Example 2 and each immersed completely for a period of 10 minutes in a dipping bath consisting of 500 ml of the solution in Examples 3 and 4. For comparison purposes a second impression of the same molding material is taken from the same patients and immersed in a solution which corresponds to the solutions in Example 3 and 4 but which does not contain the fluorine compound added according to the invention. This is then filled with dental plaster (Moldano, Bayer) as in Example 2. The plaster model produced using the impression treated according to the invention has a smooth, hard surface. There is no plaster coating left on the remaining alginate impression. With the plaster model which has been obtained using the impression not treated according to the invention, a relatively rough surface with a slightly sandy effect can be seen. On the remaining alginate impression there is a thin layer of the blue plaster material which has not hardened.

We claim:

1. A method for treating a dental model impression having a molding surface to prevent the detrimental effects of surface active substances on models produced using said surface which adhere to said dental model impression molding surfaces during cleanings, disinfecting or reducing of its surface tension,
   which comprises contacting said molding surface of said dental model with a solution containing 0.1 to 10% by weight of a fluorine compound for a time sufficient to prevent the detrimental effects of surface active substances which adhere to said molding surface of said dental model impression.

2. The method according to claim 1, wherein said solution contains 0.1 to 5% by weight of said fluorine compound.

3. The method according to claim 2, wherein said solution contains 0.5 to 2% by weight of said fluorine compound.

4. The method according to any of claims 1, 2 or 3, wherein said fluorine compound is a metal fluoride.

5. The method according to claim 4, wherein said metal fluoride is selected from the group consisting of alkali metal fluorides, magnesium fluoride, zinc fluoride, and tin fluoride.

6. The method according to any of claims 1, 2 or 3, wherein said fluorine compound is a fluorine complex.

7. The method according to claim 6, wherein said fluorine complex has the formula $A_2MF_6$, wherein A is an alkali metal and M is titanium, zirconium or hafnium.

8. The method according to claim 7, wherein said fluorine complex is $K_2TiF_6$ or $K_2ZrF_6$.

9. The method according to claim 1, wherein said contacting is affected by spraying said dental model impression with or dipping said dental model impression in said solution containing said fluorine compound.

10. The method according to claim 1, wherein said contacting further includes simultaneous disinfecting of said dental model impression with a disinfectant.

* * * * *